United States Patent [19]

Zeya

[11] Patent Number: 4,468,410
[45] Date of Patent: Aug. 28, 1984

[54] METHOD AND APPARATUS FOR PRODUCING A MICROSCOPIC SPECIMEN SLIDE

[75] Inventor: Hasan I. Zeya, Tampa, Fla.

[73] Assignee: Immunomed Corp., Tampa, Fla.

[21] Appl. No.: 409,157

[22] Filed: Aug. 18, 1982

[51] Int. Cl.³ .............................................. B05D 1/00
[52] U.S. Cl. .................................. 427/2; 118/52;
118/56; 427/4; 427/240; 427/286
[58] Field of Search ............... 118/52, 56, 730; 427/2, 427/4, 240, 286

[56] References Cited
U.S. PATENT DOCUMENTS

| 3,352,280 | 11/1967 | Hughes et al. | 118/319 |
| 3,690,290 | 9/1972 | Jarvela et al. | 118/730 |
| 3,993,018 | 11/1976 | Kranik | 118/52 |
| 3,995,022 | 11/1976 | Heanley et al. | 427/4 X |
| 4,108,109 | 8/1978 | Barger et al. | 118/52 |

Primary Examiner—Shrive P. Beck
Attorney, Agent, or Firm—Marshall, O'Toole, Gerstein, Murray & Bicknell

[57] ABSTRACT

A method and apparatus for producing a specimen slide for microscopic evaluation by spinning a slide containing a liquid sample on its surface angled 10° to 70° from the axis of rotation, whereby the centrifugal force thereby applied causes the liquid sample to form a thin streak over the slide.

30 Claims, 15 Drawing Figures

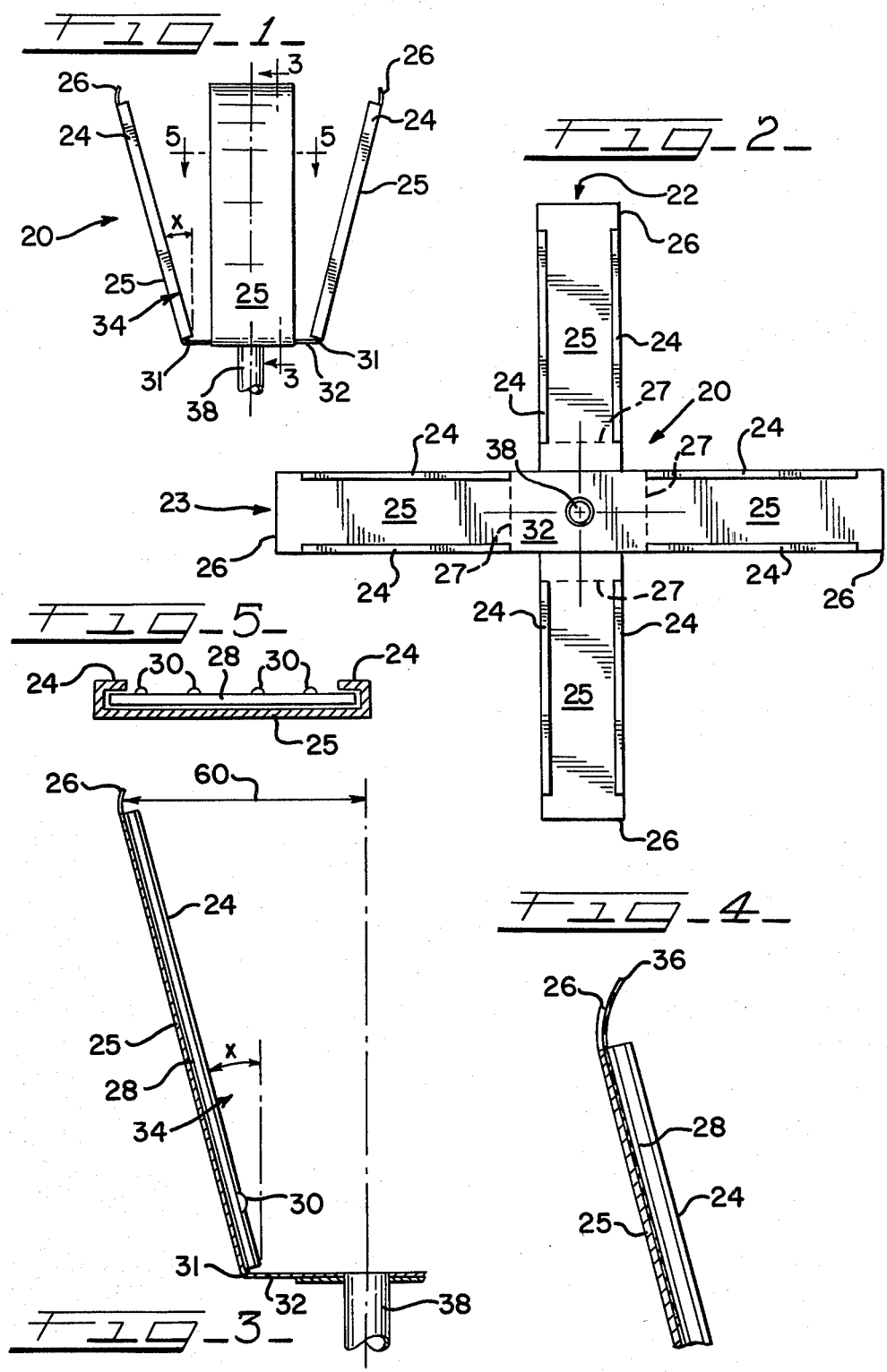

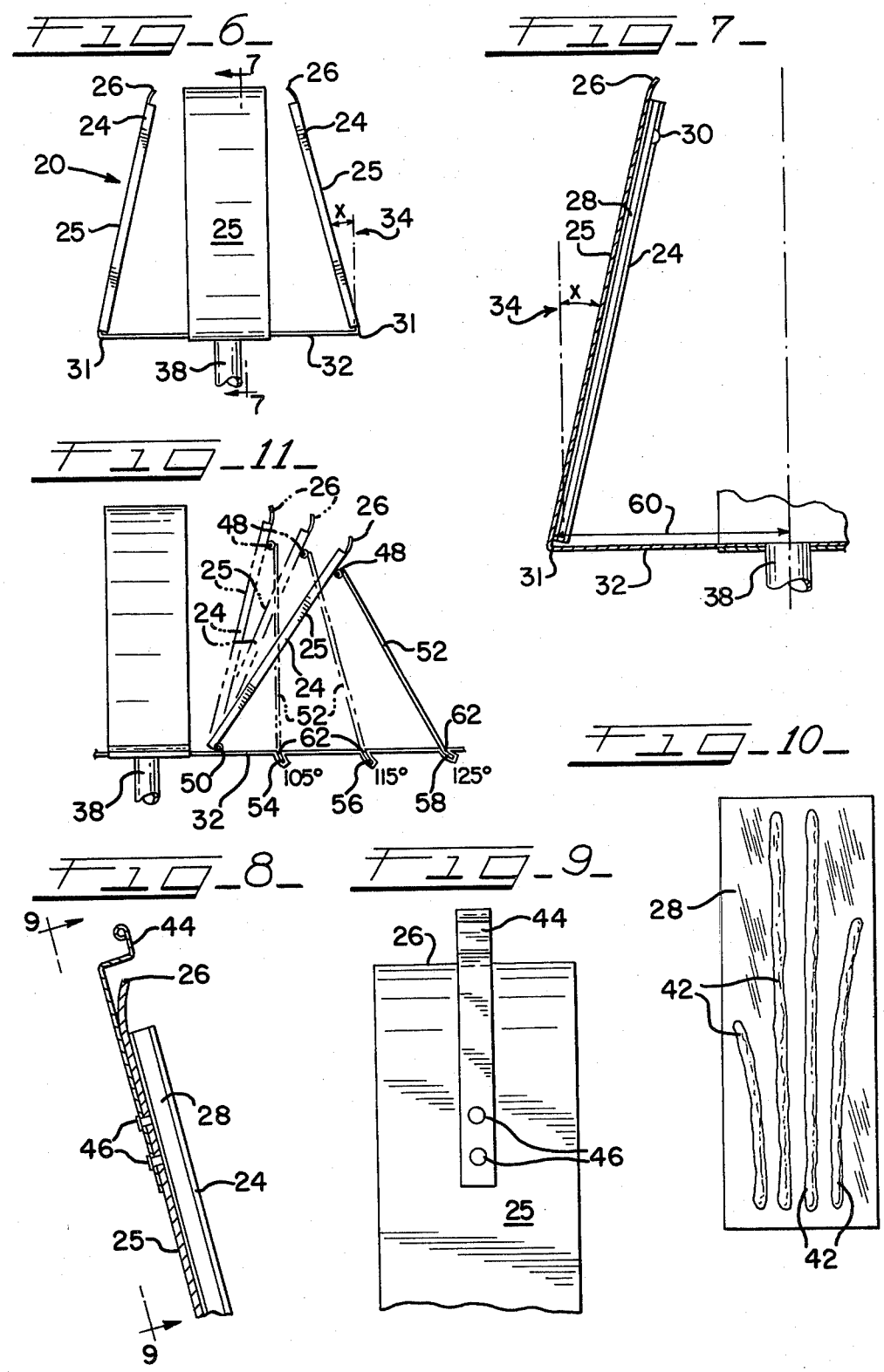

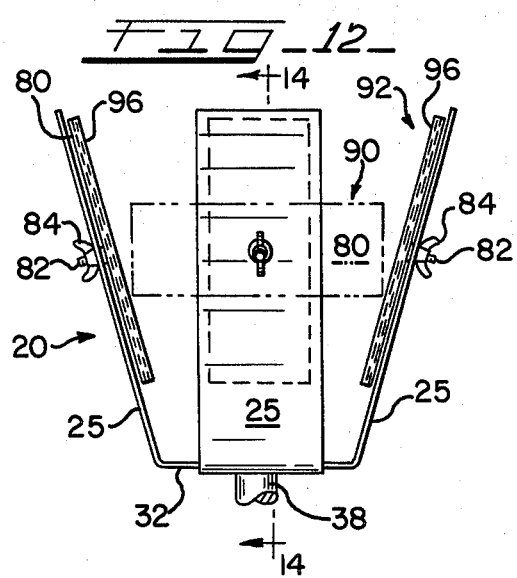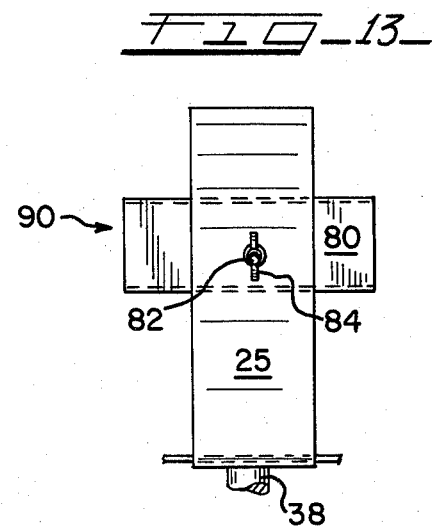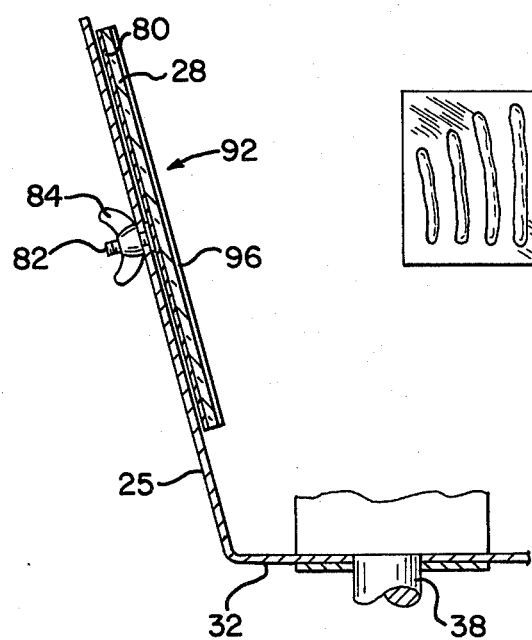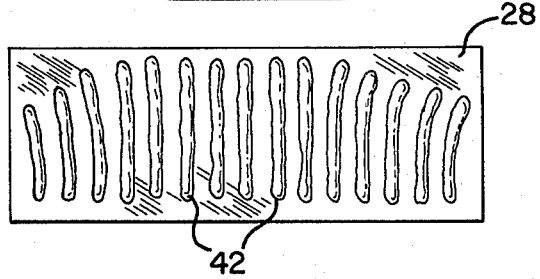

METHOD AND APPARATUS FOR PRODUCING A MICROSCOPIC SPECIMEN SLIDE

The present invention relates to a method and apparatus for preparing samples of liquids for microscopic examination and diagnostic evaluation. More particularly, this invention is concerned with an apparatus and method in which centrifugal force is applied to spread a cell-containing biological liquid sample in a thin streak of single cell thickness on an inclined slide, creating a high quality, undistorted cell smear, having a high numerical density of cells available for differential counting and morphological, histochemical, fluorescent, autoradiographic and various other types of biological tests.

BACKGROUND OF THE INVENTION

According to present laboratory practice, when it is desired to microscopically view a liquid, small samples of the liquid are placed on microscope slides in a layer as uniformly thin as a laboratory technician can achieve. While many variations of centrifuge devices for creating specimen slides for microscopic examination presently exist, problems inherent in their use have caused many laboratories, schools and research facilities to rely on the manual wedge technique of preparing liquids for microscopic examination. In this technique, two slides are used. On the first slide the sample, for example blood, is placed as a large drop. The other slide is angled toward the sample-bearing surface of the first slide until the edge of the second slide touches the sample. The second slide is then moved along the length of the first slide, literally smearing the sample over the entire surface of the first slide.

While fairly inexpensive, the manual wedge technique has many drawbacks. Only one slide can be prepared at one time, taking up valuable laboratory technician time. Excessive sample amounts are used to create the smear. Laboratory slides are wasted since only one of the two slides used in the technique is available for microscopic examination. Moreover, the number of cells per microscopic field viewable by this technique is very few.

Usually the sample on a specimen slide prepared using the wedge technique is thick. When the liquid contains cells, this hampers accurate evaluation of the morphology of the cells, which often is a critical factor in the diagnosis of diseases. As an example, in the diagnosis of leukemia it is critical to determine the number, exact type and derivation of leucocytes in the blood. Thick smears of the blood sample on a slide for microscopic examination can cause distortion in the characteristic shape of these cells, causing one cell type to be mistaken for the other. This results in false negative and false positive diagnoses of leukemia.

Additionally, the cells in the samples produced by the method are very few in number and very widely dispersed over almost the entire surface of the slide. Such a wide field for observation also creates inaccuracy and delays in performing differential counts of cell types, since the observer must constantly change the microscopic filed in all directions to examine the cells on the entire slide. Moreover, such wide dispersal also makes it almost impossible to count and identify cells, i.e., blood cells, bacterial cells, or virus particles, in patients with very low numbers of such cells. Because this procedure is slow and tedious, and because it is easy to mistakenly recount, or omit to count, a field many laboratory workers will only count a few fields rather than the entire slide. Thus, the relative number of cell types per amount of sample is frequently inaccurate, another contributing factor to misdiagnosis of the disease in question.

A further disadvantage is the relatively large amount of specimen sample required to create the specimen slide. This disadvantage is apparent in cases where the liquid in question is a biological body fluid such as blood, spinal fluid, or serum, and when the patient from whom the specimen is to be taken is either very young or very old and frail.

Methods for the production of specimen slides of liquid samples utilizing centrifugation were developed in attempts to overcome the disadvantages of the wedge technique. The prior art devices used for practicing such methods are revealed in the following patents, in which the samples are generally cell-containing biological liquids.

Johnson U.S. Pat. No. 4,294,866—Oct. 13, 1981,
Bacus U.S. Pat. No. 4,209,548—June 24, 1980,
Holroyd et al. U.S. Pat. No. 4,197,329—Apr. 8, 1980,
Barger et al. U.S. Pat. No. 4,108,109—Aug. 22, 1978,
Mikat U.S. Pat. No. 3,870,789—Mar. 11, 1975,
Staunton U.S. Pat. No. 3,705,048—Dec. 5, 1972,
Preston et al. U.S. Pat. No. 3,577,267—May 4, 1971.

The common concept upon which the methods disclosed in the above-referenced patents and devices operate is that when a slide or other sample receiving surface on which is placed a small amount of liquid is rotated with its sample-receiving surface normal to a vertical axis of rotation, centrifugal force on the sample throws off excess liquid and spreads the sample radially, forming a layer which covers approximately the entire surface of the slide.

While this concept of centrifugation solved the wedge technique problems of technician time and an excessively thick specimen layer, they also introduced other problems of their own, as well as sharing problems with the wedge technique method. These inherent problems include the danger of contamination from infectious liquids due to the radial expulsion of excess liquid from the sample placed on the slide; the chances for some distortion or disturbance of cell particle relationships due to the speed and length of time at which the slides are spun; the use of one slide for each sample; the time factor involved in subjecting only one slide at a time to centrifugation; the required sample sizes which often are difficult to obtain from elderly or infant patients; the width of the resulting smear covering the entire surface; and the current production costs of the spinning apparatus.

The danger of contamination of the surrounding atmosphere, the spinning device, the smear itself, and the distortion of the cells in the smear result from the principle of centrifugation applied in present practice. The usual size of the liquid samples required for centrifugation methods, while less than that generally needed for the wedge technique, allows for the radial expulsion of the upper excess layers during spinning to leave behind only a thin radially dispersed smear which dries as the spinner slows down. Because the centrigual force created on the slide surface spinning at a right angle to the vertical axis of rotation spreads the sample in all directions, various cell smear devices must incorporate waste capturing means such as wells to the spinner, thus increasing the complexity of the machine and its cost of production.

Distortion of cells, especially blood or bacterial cells, will result when residual liquid, upon drying, tends by surface tension to flatten the cells. In addition, the problem of creating a wide field for observation and differential counting still exists, creating the same basis for misdiagnosis as does the wedge technique.

There exists, therefore, a need for an improved method and apparatus to increase the efficiency and accuracy of preparation of liquid specimen slides for microscopic examination, particularly where the liquid is a biological cell-containing liquid, which can overcome the problems evident in the present methods of practice.

SUMMARY OF THE INVENTION

According to one aspect of the present invention there is provided a method of producing a streak of a liquid on a microscope slide, cover slip or the like. Hereafter the term "slide" is intended to refer to the ordinary rectangular glass microscope slide normally denoted by that term, and also other shapes and items, such as square or rectangular cover slips, which can be used to perform the same function. The method of the present invention comprises placing a liquid sample on one side of a slide; positioning the slide at an angle of about 10° to 70° from an axis of rotation with the face of the slide containing the liquid sample facing the axis of rotation, and with the radial distance from the sample to the axis of rotation being less than the greatest radial distance from one end of the slide to the axis of rotation; and spinning the slide around the axis of rotation so that it travels in a path which defines a truncated conical shell, whereby the centrifugal force thereby applied to the liquid sample causes the liquid to flow along the slide surface and form a thin streak thereon.

While the slide can be positioned at an angle from 10° to 70°, it is generally suitable for the slide to be positioned at an angle of 10° to 55°, and advisably 15° to 40°. It is advisable for the slide to maintain the same angle of inclination while spinning around the axis of rotation.

The speed of rotation about the axis is not narrowly critical. In the preparation of most slides about 500 to 5000 rpm, for a duration of about 0.1 to 3.0 seconds, is satisfactory, thereby creating a centrifugal force of between 500 and 2000 G. Optimal acceleration is 3000 rpm, for a duration of about 0.5 to 2.5 seconds. In general, as the slide angle increases from about 10° to 70° the speed of rotation can be decreased.

In practicing the method the liquid sample is advisably placed from near the edge or end of the slide closest to the axis of rotation to about the center of the slide. Depending upon the number of specimen samples desired to be subjected to homogeneous treatment, each slide, usually substantially rectangular in shape, can be oriented so that the longitudinal center line between its long parallel sides or the center line between its shorter parallel sides if extended would intersect the axis of rotation. It is also advisable for the slide to be substantially tangential to the conical shell which is the path in which the slide travels during rotation. Square or rectangular cover slips can also be used in place of slides in the practice of the method.

The width of the thin streak which results from spinning the slide is approximately 0.5 mm to 3 mm, so that on an average microscope slide oriented with its long parallel sides intersecting the axis of rotation between one and six samples can be deposited on the surface of the slide to form separate thin streaks on one slide. When the slides are turned so that the shorter parallel sides intersect the axis, between ten and fifteen samples may be placed on one slide. This ability to allow such large numbers of individual liquid samples to be treated simultaneously diminishes the chances that variations in cell counts and subsequent diagnosis will be due to variances in technical procedure. Additionally, one or a plurality of slides can be centrifuged simultaneously in this method.

The method of the present invention may be practiced on any liquid desired to be microscopically viewed, including for example, biological fluids containing blood cells, bacterial cells, virus particles, and the like; chemical fluids; water and colloidal suspensions. Where the liquid sample is a biological liquid containing cells, the volume of the sample suitable to provide a streak by the method can be 0.1 microliter to 5.0 microliters, with cell numbers as low as $10^2$ cells per ml or as high as $10^9$ cells per ml. Where the liquid sample is other than biological, i.e., water, colloidal suspensions or chemicals, the volume suitable for practice of this method will vary with the viscosity and density of the liquid.

The thin streak which results from application of this method applied to cell-containing biological fluid is composed of cells confined to a narrow stripe or streak for part or all of the length of the slide, with most of the liquid having flowed to the end of the slide farthest from the axis of rotation, generally leaving a streak of single-cell thickness. Excess liquid expelled from said slide by centrifugal force can be absorbed by placing any suitable means, such as an absorbent material near the edge of the slide towards which the sample flows.

According to a second aspect of this invention there is provided a rotor for a centrifuge spinning apparatus for producing specimen slides for diagnostic evaluation with a slide support member on the rotor adapted to securely hold a slide at an angle of about 10° to 70° from the axis of rotation of the rotor with the face of the slide containing the liquid sample facing the axis of rotation, and with the radial distance from the sample to the axis of rotation being less than the greatest radial distance from one end of the slide to the axis of rotation, and with the slide support member being further adapted to hold the slide so as to provide an unobstructed pathway for flow of the liquid sample on the slide surface so that spinning the rotor causes the slide to travel in a path which defines a truncated conical shell, with the slide substantially tangential to the shell so that the liquid sample can flow along the slide surface and form a thin streak thereon.

The rotor, which can contain one or a plurality of slide support members, can rotate about the axis of rotation in response to the operation of a motor capable of accelerating up to about 5000 rpm within about 0.1 second to 3.0 seconds and automatically shutting off. Optimal acceleration is about 3000 rpm, within about 0.5 second to 2.5 seconds, followed by automatic shutoff.

While the rotor will usually have one or more pairs of slide support members, it should be understood that the rotor can have one slide support member counterbalanced by suitable weight means, so that spinning of the rotor is achieved essentially free of vibration. Generally it is more convenient for the rotor to have paired opposing slide support members so that balancing can be more readily achieved. In this regard, even if only one slide is prepared, the rotor can be balanced by placing a dummy slide in the opposing slide support member.

To provide mechanical and frictional support to prevent slides from slipping out of the support members during rotation, the slide support members on the rotor can have side channels to prevent lateral displacement of the slide, and/or a flexible clip, or its equivalent, which extends over the top of said slide support members to prevent a slide from slipping out the top of said slide support member during centrifugation.

Each slide support member can also have an inwardly curved portion at the top for positioning means for absorbing excess liquid thrown off the slide during centrifugation. One or more of the slide support members can include a mechanism for adjusting the slide angle within a range of 10° to 70° from said axis. The angular adjustment can be incremented, such as in 10° to 15° increments, or it can be infinitely variable from 10° to 70°.

Additionally, each slide support member can have means for changing the orientation of a rectangular slide from a position in which the longitudinal center line between the longer sides intersects the axis of rotation to a position in which the center line between the shorter parallel sides intersects that axis. A secondary slide support member can be rotatable on said slide support member to change the slide orientation from a first position in which the longitudinal center line between the long parallel sides of the rectangular slide when extended defines a line intersecting the axis of rotation to a second position wherein the slide is rotated 90° to allow that intersecting line to be defined by the center line between the short parallel sides of a rectangular slide. This allows a greater number of specimens to be placed on one slide and subjected to uniform treatment before examination, thereby decreasing the chances of inaccuracies in counting or diagnosis. The secondary slide support member can be attached to the slide support member by a bolt or threaded screw embedded in the secondary slide support member and extending through the back of the slide support member. A securing device, such as a butterfly nut, can be used to secure the secondary slide support member in the desired position by tightening the nut which is threaded on the screw to the back of the slide support member. When a change in slide orientation is desired, the butterfly nut can be turned to loosen the secondary slide support member.

Other aspects and advantages of the present invention will become apparent upon consideration of the following detailed description.

BRIEF DESCRIPTION OF THE DRAWINGS

FIG. 1 is an elevational view of a rotor, for a centrifuge spinning apparatus, according to the invention having four slide support members;

FIG. 2 is a plan view of the rotor shown in FIG. 1;

FIG. 3 is a sectional view of a slide support member taken along line 3—3 of FIG. 1;

FIG. 4 is an enlargement of the upper part of FIG. 3;

FIG. 5 is a sectional view of a slide support member taken along line 5—5 of FIG. 1;

FIG. 6 is an elevational view of another embodiment of a rotor according to the present invention having four slide support members angled inwardly rather than outwardly as in FIG. 1;

FIG. 7 is a sectional view of a slide support member taken along line 7—7 of FIG. 6;

FIG. 8 is an enlarged sectional view of the top part of a slide support member of the present invention having a slide retaining clip;

FIG. 9 is an enlarged view of the back of the slide support member with slide retaining clip taken along line 9—9 of FIG. 8;

FIG. 10 is a top view of a slide showing four thin streaks produced by subjecting four liquid samples to the method of the present invention;

FIG. 11 is an elevational view of another embodiment of a rotor of the present invention showing means for adjustable angular movement of a slide support member;

FIG. 12 is an elevational view of another embodiment of a rotor according to the present invention showing means for changing the orientation of a rectangular slide on a slide support member;

FIG. 13 is an elevational view of a portion of the rotor of FIG. 12 showing a slide support member orienting a rectangular slide so that its short parallel sides define a line which intersects the axis of rotation;

FIG. 14 is a sectional view of a slide support member taken along line 14—14 of FIG. 12; and FIG. 15 is a top view of a slide showing fifteen thin streaks produced by subjecting fifteen liquid samples to the method of the present invention.

DETAILED DESCRIPTION

To the extent it is reasonable and practical, the same or similar elements in the various views of the drawings will be identified by the same numbers.

Referring initially to FIGS. 1, 2, and 3, indicated generally as 20 is the rotor of a centrifuge spinning apparatus for producing specimen slides for diagnostic evaluation according to the invention. The rotor 20 comprises two long, rectangular strips indicated generally at 22, 23 in FIG. 2, joined to rotatable shaft 38. One strip 23 is superimposed on the other strip 22 at a 90° angle to define four identical outwardly extending radial slide support members 25, each oriented 90° from its adjacent slide support members. The outer portions of said strips 22, 23 are bent at lateral lines 27 to define an angle X indicated generally at 34, from their axis of rotation, which is that of the rotatable shaft 38. These outer angled portions of the long, rectangular strips 22, 23 form identical slide support members 25 having channels 24 on opposing side edges spaced apart to loosely receive the opposing longitudinal edges of a conventional rectangular microscope slide 28. The center superimposed portions of said rectangular strips 22, 23 form a base 32 which rotates about the axis of rotation of rotatable shaft 38.

The top edges 26 of the slide support members 25 are curved inwardly and operate in cooperation with the channels 24 and the intersection 31 of the slide support members 25 with the base 32 to retain the slide 28 within the slide support member 25 so that during centrifugal spinning, the centrifugal force exerted will not force the slide 28 out of the slide support member 25.

In FIGS. 1, 3, 6 and 7, slide support members 25 are positioned at an angle X, 34, from the axis of rotation of rotatable shaft 38, which in FIG. 1 is a vertical axis of rotation although the axis can be horizontal or any angle between vertical and horizontal. In the practice of the present invention, angle X is within the range of angular movement between 10° and 70° from the axis of rotation of the rotatable shaft 38.

FIG. 3 shows one orientation of a slide support member 25 and slide 28 when the slide 28 is positioned in the slide support member 25 in preparation for centrifugal spinning. Slide 28 is oriented on the slide support member 25 with the surface of the slide 28 containing the liquid sample 30 facing the axis of rotation of rotatable shaft 38. The radial distance from the sample 30, on the lower end of the slide 28, to the shaft 38 is less than the greatest radial distance 60 from the upper end of the slide 28 to the shaft 38, so that the spinning of the rotor 20 will cause the slide 28 to travel in a path which defines a truncated conical shell. When slide 28 in slide support member 25 is subjected to a speed of rotation of between 500 and 3000 rpm for 0.5 to 2.5 seconds, a centrifugal force of 500 to 1000 G is created. The centrifugal force causes the liquid sample 30 to flow along all or part of the length of the slide 28, forming a narrow, thin streak 42, as seen in FIG. 10.

Referring to FIG. 4, an alternative embodiment of the slide support member 25 is shown. A piece of absorbent filter paper 36 rests between the slide support member 25 and the slide 28. The curved top 26 of the slide support member 25 functions to direct the pliable filter paper 36 in a tilted direction above the surface of slide 28 so that any excess liquid sample which is thrown off by centrifugal spinning will be captured and absorbed by the curved area of filter paper 36. This is a particularly important function where said sample is an infectious sample, such as a bacterial culture or a blood or water sample containing infectious microorganisms. Unlike prior methods, however, such a small amount of sample 30 is used to create a streak 42, that very little will be expelled from the slide 28. In addition, since the centrifugal force is applied in one direction to create a streak 42, no radial waste expulsion should occur.

Another advantage of the present invention is that a plurality of sample specimens 30 may be streaked on one slide 28. Because the centrifugal force causes each sample 30 to flow in primarily one direction, the streaks 42 will not overlap. FIG. 5, a cross-section of the slide support member 25 holding the slide 28, shows four spaced apart liquid samples 30 on the surface of the slide 28 which faces the rotatable shaft 38. Upon spinning the slide 28, streaks 42 are obtained on it as shown in FIG. 10.

FIG. 6 shows an alternate orientation of slide support members 25 on the rotor indicated generally at 20. Slide support members 25 are shown to have an angle X from their axis of rotation, or rotatable shaft indicated at 38. The angle X shown in the drawings is 15°. The same principles of centrifugal force apply in this embodiment, since the centrifugal force acts on a sample 30 positioned on an inclined surface as seen in FIG. 7, which is a sectional view of slide support member 25. Liquid sample 30 is positioned on the surface of slide 28 facing the rotatable shaft 38, but at the upper part of the slide 28. Despite the orientation, however, the liquid sample 30 is still at a position where the radial distance from the sample 30 to the shaft 38 is less than the greatest radial distance 60 from one end of the slide 28 to the shaft 38. Again, spinning of the rotor 20 causes the slide 28 to travel in a path which defines a truncated conical shell, so that the liquid sample 30 can flow along the slide surface and form a thin streak 42 thereon.

FIG. 8 illustrates another embodiment of slide support member 25. In this Figure, which is an enlarged section of the top part of a slide support member 25, there is fastened onto the back of the slide support member 25 a flexible clip 44. The flexible clip 44 functions as additional retention means to prevent slide 28 from flying from out the top of slide support member 25 during centrifugal spinning. The flexible clip 44 is preferably formed of thin, flexible steel, so that it is able to be pressed towards the slide support member 25 out of the path of insertion and removal of the slide 28 into the slide support member 25. In FIG. 9, the flexible clip 44 is seen from the back view, where the rivets 46, which hold the clip 44 onto the back of the slide support member 25, may clearly be seen.

FIG. 10 shows the end result of the use of the method and apparatus of the present invention. In the method, a plurality of sample specimens 30 are dotted on the slide 28, as shown in FIG. 5, and then subjected to centrifugal spinning at an angle X, 34, from the axis of rotation of rotatable shaft 38. The resulting centrifugal force acting on the specimen sample 30 lying on an inclined plane spreads the sample 30 in a thin streak 42 along the length of the slide 28. FIG. 10 shows four such streaks 42, resulting from subjecting four liquid samples 30 as in FIG. 5 on one slide 28 to the method of the present invention, thereby allowing exposure of the samples to uniform testing conditions.

FIG. 11 shows an alternative embodiment of a slide support member 25 on a rotor indicated generally at 20. The slide support member 25 is adapted for adjustable angular movement by means of a leg 52 attached to the back of the slide support member 25 by means of a hinge 48. The slide support member 25 is attached for adjustable movement to the base 32 of the rotor 20. The base 32 extends beyond the slide support member 25 in this embodiment. Positioned at stated points along the base 32 are slots 54, 56, and 58, for receiving the foot 62 of the adjustable leg 52. When the foot 62 is inserted into the slot 54, angle X defines an angle of 15° from the axis of rotation of rotatable shaft 38. When the foot 62 is inserted into the slot 56, angle X of slide support member 25 from the shaft 38 is 25°. In this example, when foot 62 is inserted into slot 58, angle X reaches 35° from the shaft 38. These adjustment means provide for differences in flowability of individual liquid samples. The greater the degree of inclination of the angle X, the easier and quicker is the streak formed on the inclined slide 28 held within the slide support member 25.

FIG. 12 shows aother embodiment of the rotor of the present invention in which slide support members 25 also provide means for changing the orientation of a rectangular slide to encompass a greater number of specimens. Attached to said slide support members 25 are secondary slide support members 80 which are rotatable from a first position indicated generally at 92 in FIGS. 12 and 14 in which a rectangular slide is held so that its longer parallel sides define a line which intersects the axis of rotation represented by rotatable shaft 38 to a second position indicated generally at 90 in FIG. 13 and in dotted lines in FIG. 12 in which said secondary slide support member 80 holds a rectangular slide so that the short parallel sides of the rectangular slide define the line which intersects the axis of rotation 38. Said secondary slide support member 80 is joined to the slide support member 25 by a bolt 82 which extends from the secondary slide support member 80 through the back of the slide support member 25. Said bolt 82 is releasably tightened by butterfly nut 84 to hold said secondary slide support member 80 in said first or said second positions, 92 and 90 respectively.

Shown most cleraly in FIG. 14, said secondary slide support member 80 has channels 96 on opposing edges of said secondary slide support member 80 spaced apart to loosely receive the opposing longitudinal edges of a conventional rectangular microscope slide 28. When it is desired to place between ten and fifteen specimen samples on one slide to ensure homogeneous treatment of said samples, the secondary slide support member 80 can be rotated from its first position 92 illustrated in FIG. 14 by loosening butterfly nut 84, turning said secondary slide support member 80 to the second position 90, illustrated in FIG. 13, and turning butterfly nut 84 tightly against slide support member 25 to maintain the position of secondary slide support member 80 during centrifugation.

FIG. 15 shows the end result of the use of the method and apparatus of the present invention in the embodiment of FIG. 12 having means to change the orientation of a rectangular slide 28.

In the method, a plurality of sample specimens are dotted on slide 28 and then subjected to centrifugal spinning and an angle X, 34, from the axis of rotation of rotatable shaft 38, the secondary slide support member 80 being in the second position 90 illustrated in FIG. 13. Resulting centrifugal force acts on the specimen samples lying on an inclined plane to spread the samples in thin streaks 42 along the surface of the slide 28. FIG. 15 shows fifteen such streaks 42 resulting from subjecting fifteen liquid samples on one slide 28 in the second secondary slide support member position 90 in which the shorter parallel sides of slide 28 when in the secondary slide support member 80 define a line which would intersect the axis of rotation.

The following example illustrates use of the method and apparatus of the present invention with a biological cell-containing liquid, blood.

EXAMPLE 1

Using the centrifuge spinner with a rotor as illustrated in FIG. 1 of the drawing, two slides are prepared for microscopic examination of a blood sample. Four drops of blood sample containing approximately $10^4$ cells per cubic millimeter are deposited near the bottom end of slide A, the drops being equally spaced from each other across the width of the slide. The same procedure is followed for slide B.

Each slide is slipped into one opposing slide support member of the rotor beneath the grip of the channels which line the longitudinal length of the slide support members. Filter paper sections are placed on the curved tips of the slide support members which curve the filter paper slightly over the top of each slide. The slides are positioned in the opposing slide support members so that the drops of blood are closer to the base of the rotor. The slide support members in this rotor are angled 15° from the axis of rotation. The rotor is powered by a conventional motor and set to achieve 2000 rpm for 1.5 seconds, creating a force of gravity of about 700 G.

After the slides are spun, they are removed from the slide support members. The filter paper is also removed and discarded. Each slide now has four narrow streaks of blood sample which extend approximately the entire length of the slide.

The slides, stained with appropriate dyes and cytochemical reagents, are inserted onto the base of a microscope and examined at a magnitude of 400, in which three microscope fields are seen at once. On examining the individual streaks, the laboratory technician is able to follow the length of the streak, since under this magnification the entire width of each streak can be observed. Observable in each streak are the individual blood cells which can be differentiated by their characteristic morphology. Since the cells are spread in a single layer and the number of cells per oil immersion field is high (10–15 cells per field in contrast to 1–2 cells per field by wedge technique), it is quite easy to count the number of cells per sample drop by moving the platform of the microscope in one direction to follow the length of each streak formed. Both slides are examined by this method and differential counts are made quickly and easily.

While only a limited number of embodiments of the present invention have been disclosed herein, it will be readily apparent to persons skilled in the art that numerous changes and modifications may be made thereto without departing from the spirit of the invention.

What is claimed is:

1. A method of producing a streak of a liquid on a microscope slide, cover slip or the like, which method comprises:

placing a liquid sample on one side of a slide;

positioning the slide at an angle of about 10° to 70° from an axis of rotation with the face of the slide containing the liquid sample facing the axis of rotation, and with the radial distance from the sample to the axis of rotation being less than the greatest radial distance from one end of the slide to the axis of rotation; and spinning said slide around the axis of rotation while maintaining said angle so that it travels in a path which defines a truncated conical shell;

whereby the centrifugal force thereby applied to the liquid sample causes the liquid to flow along the slide surface and form a thin streak thereon.

2. The method of claim 1 wherein the slide is substantially tangential to the truncated conical shell defined by the path of the rotating slide.

3. The method of claim 1 wherein the duration of spinning time comprises from about 0.1 to 3.0 seconds.

4. The method of claim 1 wherein the duration of spinning time comprises from about 0.5 to 2.5 seconds.

5. The method of claim 1 or 2 wherein said centrifugal force is between 500 and 2000 G.

6. The method of claim 1 or 2 wherein the speed of rotation is between 500 and 5000 rpm.

7. The method of claim 1 wherein the width of said thin streak is approximately 0.5 mm to 3 mm.

8. The method of claim 1 wherein between one and fifteen samples are deposited on the surface of said slide to form separate thin streaks on the slide.

9. The method of claim 1 wherein a plurality of slides is centrifuged simultaneously.

10. The method of claim 1 wherein said liquid sample is placed near the edge of said slide closest to the axis of rotation.

11. The method of claim 1 wherein said slide is substantially rectangular in shape and oriented so that its longitudinal center line intersects the axis of rotation.

12. The method of claim 1 wherein said slide is substantially rectangular in shape and oriented so that its shorter parallel sides define a line which intersects the axis of rotation.

13. The method of claim 1 wherein said liquid is a biological liquid containing cells.

14. The method of claim 13 wherein said cells are a member of the group comprising blood cells, tissue cells, bacterial cells.

15. The method of claim 1 wherein said liquid is a biological liquid containing viral particles.

16. The method of claim 1 wherein the volume of said sample comprises between 0.1 microliters to 5 microliters, and cell numbers between $10^2$ cells per ml to $10^9$ cells per ml.

17. The method of claim 1 wherein said thin streak is composed of cells distributed along the length of the streak, with much of the liquid flowing to the end of the slide farthest from the axis of rotation, leaving a streak of single-cell thickness with high numbers of cells per microscopic field.

18. The method of claim 1 wherein excess liquid expelled from said slide by centrifugal force is absorbed by placing absorbent material near the edge of the slide towards which the sample flows.

19. A centrifuge spinning apparatus having a rotor for producing specimen slides for diagnostic evaluation comprising:
a slide support member on the rotor adapted to securely hold a slide only at an angle of about 10° to 70° from the axis of rotation of the rotor and so that the slide cannot rotate through the vertical to a different angle and with the face of the slide containing a liquid sample facing the axis of rotation, and with the radial distance from the sample to the axis of rotation always being less than the greatest radial distance from one end of the slide to the axis of rotation so that spinning the rotor causes the slide to travel in a path which defines a truncated conical shell, so that the liquid sample can flow along and for the length of the slide surface and form a thin streak thereon and excess liquid sample can flow unobstructedly off the slide; and,
an inwardly curved portion on said slide support member for positioning means for absorbing excess liquid thrown off said slide during centrifugation.

20. The apparatus of claim 19 further comprising:
a portion of a flexible clip attached to said slide support member which extends over said inwardly curved portion of said slide support member for preventing a slide from slipping out the top of said slide support member during centrifugation.

21. A centrifuge spinning apparatus having a rotor for producing specimen slides for diagnostic evaluation comprising:
a slide support member on the rotor adapted to securely hold a slide only at an angle of about 10° to 70° from the axis of rotation of the rotor and so that the slide cannot rotate through the vertical to a different angle and with the face of the slide containing a liquid sample facing the axis of rotation, and with the radial distance from the sample to the axis of rotation always being less than the greatest radial distance from one end of the slide to the axis of rotation so that spinning the rotor causes the slide to travel in a path which defines a truncated conical shell, so that the liquid sample can flow along and for the length of the slide surface and form a thin streak thereon and excess liquid sample can flow unobstructedly off the slide; and
said slide support member being attached to said rotor for angular adjustable movement within a range of 10° to 70° from said axis.

22. A centrifuge spinning apparatus having a rotor for producing specimen slides for diagnostic evaluation comprising:
a slide support member on the rotor adapted to securely hold a slide at an angle of about 10° to 70° from the axis of rotation of the rotor with the face of the slide containing the liquid sample facing the axis of rotation, and with the radial distance from the sample to the axis of rotation being less than the greatest radial distance from one end of the slide to the axis of rotation so that spinning the rotor causes the slide to travel in a path which defines a truncated conical shell, so that the liquid sample can flow along the slide surface and form a thin streak thereon;
means for changing the angular orientation of said slide when positioned in said slide support member; and
a secondary support member rotatable on said slide support member about a center pivot from a first position in which the longitudinal center line of a slide intersects the axis of rotation to a second position in which a center line parallel to the shorter parallel sides of a slide defines a line intersecting said axis of rotation.

23. The apparatus of claim 22 further comprising:
means for securing said secondary support member in said first and second positions.

24. A centrifuge spinning apparatus for producing a specimen slide having a thin streak of a liquid sample thereon for diagnostic evaluation comprising:
a rotor having an axis of rotation;
a slide support member on said rotor adapted to securely position a slide only at an angle of about 10° to 70° from said axis of rotation and so that the slide cannot rotate through the vertical to a different angle and with the face of the slide containing a liquid sample facing said axis, and with the radial distance from the sample to said axis always being less than the greatest radial distance from one end of the slide to said axis;
means for spinning said rotor causing said slide to travel in a path which defines a truncated conical shell; and
said slide support member being further adapted to hold the slide so as to provide an unobstructed pathway for flow of said liquid sample on the slide, whereby when said rotor is spinning, said liquid sample can flow along and for the length of said slide in a thin streak and excess liquid sample can flow unobstructedly off the slide.

25. The apparatus of claim 24 wherein said slide support member holds said slide in a substantially tangential position to the truncated conical shell defined by said slide's path during spinning of said rotor.

26. The apparatus of claim 24 further comprising:
a plurality of said slide support members.

27. The apparatus of claim 24 wherein said slide support member comprises:
parallel slide receiving channels for providing mechanical and frictional support to prevent a slide from slipping off said support member during spinning of said rotor.

28. The apparatus of claim 24 further comprising:

means for changing the angle of said slide from between about 10° to about 70° from said axis of rotation when said slide is positioned in said slide support member.

29. A centrifuge spinning apparatus for producing a specimen slide having a thin streak of a liquid sample thereon for diagnostic evaluation comprising:
a rotor having an axis of rotation;
a slide having a liquid sample on one of its faces;
a slide support member on said rotor adapted to securely position said slide only at an angle of about 10° to 70° from said axis of rotation and so that the slide cannot rotate through the vertical to a different angle and with the face of the slide containing a liquid sample facing the axis of rotation, and with the radial distance from the sample to the axis of rotation always being less than the greatest radial distance from one end of the slide to the axis of rotation;
means for spinning said rotor and causing said slide to travel in a path which defines a truncated conical shell; and
said slide support member being further adapted to hold the slide so as to provide an unobstructed pathway along said slide for flow of said liquid sample on the slide, whereby when said rotor is spinning, said liquid sample can flow along and for the length of the slide surface in a thin streak and excess liquid sample can flow unobstructedly off the slide.

30. The apparatus of claim 29 further comprising:
a plurality of said slide support members;
slide receiving channels on said slide support member for providing mechanical and frictional support to prevent a slide from slipping off said support member during rotation of said rotor;
an inwardly curved portion on said slide support member for positioning means for absorbing excess liquid thrown off the slide during centrifugation;
means for imparting to said slide support member angular adjustable movement within a range of 10° to 70° from said axis;
a portion of a flexible clip attached to said slide support member which extends over said inwardly curved portion of said slide support member for preventing a slide from slipping out the top of said slide support member during centrifugation;
a secondary support member rotatable on said slide support member about a center pivot from a first position in which the longitudinal center line of a slide intersects the axis of rotation to a second position in which the shorter parallel sides of a slide define a line intersecting said axis of rotation; and
means for securing said secondary support member in said first and second positions.

* * * * *